US007186874B2

(12) United States Patent
Dakka et al.

(10) Patent No.: US 7,186,874 B2
(45) Date of Patent: Mar. 6, 2007

(54) PROCESS FOR THE OLIGOMERIZATION OF OLEFINS

(75) Inventors: Jihad Mohammed Dakka, Whitehouse Station, NJ (US); Hans K. T. Goris, Laakdal (BE); Georges M. K. Mathys, Bierbeek (BE); Roger Eijkhoudt, GC Breda (NL); Marc P. H. Puttemans, Dilbeek (BE); Stephen Harold Brown, Brussels (BE)

(73) Assignee: ExxonMobil Chemical Patents Inc., Houston, TX (US)

( * ) Notice: Subject to any disclaimer, the term of this patent is extended or adjusted under 35 U.S.C. 154(b) by 77 days.

(21) Appl. No.: 10/492,705

(22) PCT Filed: Oct. 23, 2002

(86) PCT No.: PCT/GB02/04776

§ 371 (c)(1),
(2), (4) Date: Sep. 8, 2004

(87) PCT Pub. No.: WO03/035584

PCT Pub. Date: May 1, 2003

(65) Prior Publication Data

US 2005/0014630 A1  Jan. 20, 2005

(30) Foreign Application Priority Data

Oct. 24, 2001 (EP) .................................. 01309013
Oct. 24, 2001 (EP) .................................. 01309032

(51) Int. Cl.
*C07C 2/02* (2006.01)
(52) U.S. Cl. ........................ 585/533; 585/502; 585/520
(58) Field of Classification Search ................ 585/502, 585/520, 533
See application file for complete search history.

(56) References Cited

U.S. PATENT DOCUMENTS

| 4,556,477 A | 12/1985 | Dwyer ........................ 208/111 |
| 4,973,870 A | 11/1990 | Uehara ........................ 310/78 |
| 5,157,201 A * | 10/1992 | Norris ........................ 585/820 |

FOREIGN PATENT DOCUMENTS

| EP | 0 174 121 | 5/1992 |
| EP | 0 746 538 | 1/1999 |
| WO | 93/16020 | * 8/1993 |
| WO | WO 93/25475 | 12/1993 |
| WO | WO 94/12452 | 9/1994 |
| WO | WO 95/22516 | 8/1995 |

\* cited by examiner

*Primary Examiner*—Glenn Caldarola
*Assistant Examiner*—In Suk Bullock
(74) *Attorney, Agent, or Firm*—Andrew B. Griffis

(57) ABSTRACT

Sulphur-containing olefinic feedstocks are oligomerized over zeolite catalysts.

23 Claims, No Drawings

US 7,186,874 B2

PROCESS FOR THE OLIGOMERIZATION OF OLEFINS

CROSS-REFERENCE TO RELATED APPLICATIONS

This application is the U.S. National Stage of International Application No. PCT/GB02/04776, filed Oct. 23, 2002 which claims priority to European patent application no. 01309013.9, filed Oct. 24, 2001 and European patent application 01309032.9, filed Oct. 24, 2001.

FIELD OF THE INVENTION

This invention relates to a process for the manufacture of higher molecular weight organic molecules from lower molecular weight materials, especially olefins, by oligomerization, to crystalline molecular sieves suitable for use in the process, and the use of such molecular sieves in such reactions. The invention also relates to the oligomers produced and their use as feedstocks for further reactions.

DESCRIPTION OF RELATED ART

Molecular sieve catalysts of many types have been used, or proposed for use, in numerous chemical processes. Commercially, they have been used, for example, in hydrocarbon dewaxing, hydrocracking, toluene disproportionation, and alkylation of aromatics. Among processes for which they have been proposed in the literature is the conversion by oligomerization of lower olefins, e.g., alkenes, to higher olefins, e.g., higher alkenes, for example the oligomerization of $C_2$ to $C_6$, especially $C_3$ and $C_4$, olefins to olefins in the $C_6$ to $C_{12}$ range, and occasionally higher.

An example of a proposal to use crystalline molecular sieves as catalysts for oligomerization is that described in EP-B-625 132, where a hydrated olefinic feedstock is oligomerized over a zeolite catalyst, the water content of the feedstock being from 0.05 to 0.25 molar percent. The process is said to result in an increase in yield of higher molecular weight alkenes and to have the additional advantage of enabling the reaction to be carried out at relatively low temperatures. Another example of such a proposal is that described in EP-B-746 538, where zeolites of the structure types MFI, TON, and MFS, in their acid forms, are used in oligomerization of propene and butene, the particular members of those structure type families used being ZSM-5, ZSM-22, and ZSM-57. The patent is concerned with controlling the extent of oligomerization, to obtain the desired proportions of or selectivity to dimer, trimer, and higher oligomers, for use in downstream manufacturing processes. In the patent, methods of improving trimer yield are described, the observation being made that higher conversion rates produce an oligomer mixture with a lower degree of branching.

The use of crystalline molecular sieves as catalysts has been found, however, to be subject to certain limitations in practice. The feedstocks used are frequently refinery products and may contain sulphur compounds. In commercial processes customarily using such feedstocks as, for example, alkylation of aromatics and toluene disproportion sulphur has to be removed before the feedstock contacts the catalyst. Exceptionally, if the feed contains hydrogen as, for example, in dewaxing and hydrocracking, sulphur removal may not be necessary as the hydrogen present appears to stabilize the catalyst.

SUMMARY OF THE INVENTION

Our experiments have shown that under conditions normally used for olefin oligomerization over molecular sieve catalysts, sulphur-containing feedstocks may reduce catalyst activity and lifetime. However, it has now surprisingly been found that the presence of sulphur does not appear to have adverse effects on the reaction process itself. Indeed, provided oligomerization is carried out at a temperature higher than that which would otherwise have been chosen for the reaction concerned, the effect on catalyst activity and life may be mitigated, minimal, or even of advantage.

The temperature appropriate to mitigate the adverse effects of sulphur compounds will vary, depending on the catalyst being used, the olefinic species being oligomerized, the specific sulphur compound or compounds and their proportions present in the feedstocks. An appropriate minimum temperature may, however, be readily identified by routine experiment.

DESCRIPTION OF THE INVENTION

The present invention accordingly provides a process for the oligomerization of an olefinic feedstock which comprises contacting under oligomerization conditions an olefinic feedstock comprising sulphur-containing compounds at an elevated temperature with a catalyst comprising at least one crystalline molecular sieve selected from sieves having the TON and MFS structure types, and recovering a product containing at least one olefin oligomer.

In this specification, the term "structure type" is used in the sense described in the Structure Type Atlas, Zeolites 17, 1996. Examples of TON structure type zeolites include ZSM-22, ISI-1, Theta-1, Nu-10, and KZ-2, and of MFS include ZSM-57, all preferably in their H- or acid form.

The crystalline molecular sieve is advantageously ZSM-22 or ZSM-57. ZSM-22 and its manufacture are described in, for example, U.S. Pat. No. 4 556 477 and WO 93/25475, and ZSM-57 and its manufacture in EP-A-174 121 and U.S. Pat. No. 4 973 870, the disclosures of all of which are incorporated herein by reference. Mixtures of two or more molecular sieves may be used, e.g., a mixture of ZSM-22 and ZSM-57.

A molecular sieve crystallite size advantageously up to 5 μm, preferably within the range of from 0.05 to 5 μm, more especially from 0.05 to 2 μm, and most preferably from 0.1 to 1 μm, may be employed. The molecular sieve may be supported or unsupported, for example in powder form, or used as an extrudate with an appropriate binder. An as-synthesized molecular sieve is advantageously converted to its acid form, for example by acid treatment, e.g., by HCl, or by ammonium ion exchange, and subsequent calcination before use in the process of the invention. The calcined materials may be post-treated as by steaming. Although the invention will be described with reference to zeolites proper, it is possible to use, as is known in the art, a material in which silicon and aluminium have been replaced in whole or in part by other elements, silicon more especially by germanium or phosphorus and aluminium more especially by boron, gallium, chromium and iron, materials containing such replacement lattice elements also being termed zeolites, and the term is used in the broader sense in this specification.

The olefin feedstock advantageously contains olefins having from 2 to 12 carbon atoms, preferably from 2 to 6 carbon atoms, and is advantageously an alkene-containing feedstock. The feedstock itself may be or comprise an oligomer, especially a dimer, especially one provided by recycling a part of a product stream. The feed preferably contains propene, butenes, pentenes and/or hexenes; the invention is especially applicable to propene and butene oligomerization.

As indicated above, the feedstock contains sulphur-containing compounds. The feedstock advantageously contains within the range of from 1 to 100, more advantageously up to 50, still more advantageously up to 30, preferably up to 20, more preferably up to 5, and still more preferably up to 2, ppm by volume of such compounds. It is within the scope of the invention to reduce the proportion of sulphur compounds from above the upper end of any of the given ranges, for example about 200 ppm, to within any of the ranges, and also to reduce the proportion from within a less preferred range to a more preferred range. A typically encountered feedstock may have from 1 to 30 or from 2 to 20 ppm by volume of sulphur compounds, and the invention is well suited to such feedstocks.

The sulphur content is conveniently ascertained by gas chromatographic analysis using peak areas normalized with reference to a COS standard.

As examples of sulphur-containing compounds, there may be mentioned, more especially, saturated aliphatic compounds, for example, thiols, sulphides, including cyclic sulphides, and disulphides. Typical compounds include, for example, hydrogen sulphide, dimethyl sulphide, diethyl sulphide, ethyl methyl sulphide, n-propyl sulphide, 1- and 2-propanethiols, 1-butanethiol, 1,1-methylethylthiol, ethyl methyl disulphide, dimethyl disulphide and tetrahydrothiophene.

Reaction conditions for the process of the invention may be, with the exception of the temperature and the presence of the sulphur compound or compounds, in accordance with conditions operative for prior art processes for oligomerization of the same olefin or olefins.

The olefinic feedstock may be fed to the reaction zone in the liquid or, preferably, the supercritical phase. The feedstock may contain water, either present from the feedstock raw material or by addition.

The feedstock advantageously comprises from 0.05 to 0.25, preferably from 0.06 to 0.20 and more preferably from 0.10 to 0.20, molar % water based on the total hydrocarbon content of the feedstock. If desired or required, the natural water content of the feedstock may be increased, for example, by being passed through a thermostatted water saturator. Since the amount of water required to saturate the feedstock will depend upon the temperature and composition of the feedstock, control of the water content may be effected by appropriate control of the temperature of the feedstock.

The feedstock may also comprise an inert diluent, for example, a saturated hydrocarbon. That other hydrocarbon is included in the hydrocarbon content for the purposes of calculation of the water content.

Operating temperatures for olefin oligomerization have variously been reported in the literature as being between 80° C. and 350° C. Toward and above the upper end of the range, de-oligomerization rates increase and may predominate over the oligomerization reaction, providing the upper limit to practical operation.

As indicated above, once the person skilled in the art is in possession of the invention, it is a matter of routine experiment to ascertain, for a given feedstock and catalyst, the minimum and optimum temperatures for operation within the general ranges of 100° C. to 350° C., especially 135° C. to 350° C. and more especially 150° C. to 300° C. In general, a temperature of at least 160° C. has been found advantageous. The following combinations are given as examples only.

In MFS (typically ZSM-57) catalysed reactions, an operating temperature of at least 160° C. and up to about 220° C. is advantageous, at least 170° C. is preferred, and at least 200° C. is more preferred. An MFS catalyst is preferred when the feedstock is propene and the target oligomers are nonenes.

In TON (typically ZSM-22)-catalysed reactions, an operating temperature of at least 190° C., preferably 200° C., is advantageous, at least 220° C. is preferred, and at least 250° C. is more preferred. An advantageous upper limit is 350° C.; a preferred upper limit is 300° C. A TON catalyst is preferred when the feedstock is butene and the target oligomers are low-branched octenes.

It will be appreciated that, to maintain desirable conversion rates, it may be advantageous to increase reaction temperatures with the time the catalyst is on stream.

The pressure is advantageously in the range of 5 to 10 MPa, preferably from 6 to 8 MPa. The olefin hourly space velocity is advantageously in the range of from 0.1 to 20, preferably from 1 to 10, and more preferably from 1.5 to $7.5, hr^{-1}$.

When the oligomer product is to be used as starting material for certain purposes, e.g., in the manufacture of certain plasticizer or detergent grade alcohols, it is desirable to minimize the degree of branching of the product.

The degree of branching of the olefin oligomer may be controlled to some extent by operating temperature, higher temperatures normally yielding a lower degree of branching (branchiness). The olefin branchiness largely determines that of any downstream product, for example plasticizer or detergent grade alcohols, produced, for example, by the oxo process, from the oligomer olefins. The users of such products, and in turn their downstream products, for example plasticizer esters, have strict specifications for various properties which the suppliers have to meet, and these specifications typically require branchiness to be within a defined range, usually a low range.

However, when an oligomerization operation is started up using fresh catalyst, the catalyst is highly active and, since the oligomerization is exothermic, there is a serious risk of reactor runaway. It is therefore normally necessary to operate initially at a low temperature and only reach the desired operating temperature over a prolonged period, during which substantial quantities of product are produced. This portion of the product will be of greater branchiness than that produced later, thereby increasing the average branchiness of the product, increasing the difficulty of meeting the customer's specification.

It has surprisingly been found that using a sulphur-containing feed as described herein in some way controls the initial over-activity of the catalyst, enabling the reaction to be started up at, or close to, the desired operating temperature.

The invention accordingly also provides a process for controlling the activity in an oligomerization reaction of a catalyst comprising at least one crystalline molecular sieve selected from sieves of the TON and MFS structure types, which comprises contacting the molecular sieve with a sulphur compound-containing olefinic feedstock.

The invention accordingly also provides a process for controlling the degree of branching of the product of an oligomerization reaction which comprises contacting under oligomerization conditions a sulphur compound-containing olefinic feedstock with a catalyst comprising at least one crystalline molecular sieve selected from sieves having the TON and MFS structure types.

The invention accordingly also provides the use of an elevated temperature in such a reaction to control the degree of branching of the oligomeric product.

Advantageously, the sulphur content of the feedstock is from 1 to 100 ppm by volume.

The effect on the degree of branching is especially evident when the feedstock is propene; with ZSM-22, the branchiness of the trimer is significantly reduced; with ZSM-57, branchiness of both dimer and trimer is reduced.

The present invention also provides a crystalline molecular sieve of the TON or MFS structure type having absorbed therein or adsorbed thereon at least one sulphur-containing compound. Advantageously, the crystalline molecular sieve is ZSM-22 or ZSM-57. Advantageously, the sulphur compound is, or is derived from, one of the groups specified above, and preferably is, or is derived from, one of the specific compounds identified above. Advantageously, the crystalline molecular sieve having a sulphur-containing compound absorbed therein or adsorbed thereon is one obtainable by, and preferably one obtained by, use as an oligomerization catalyst for a sulphur compound-containing feedstock.

The oligomers produced by the process of the present invention are a unique mixture of isomers, the members of which fall into five types of skeletal structures, which are Type I $CH=CH_2$
Type II $CH=CHR'$
Type III $RRC=CH_2$
Type IV $RR'C=CHR''$
Type V $RR'C=CR''R'''$ where R, R', R" and R'" are alkyl groups. The olefin type may be identified by proton NMR analysis. Especially in combination with the controlled average degree of branching, the oligomer products of the invention have advantages over those produced by traditional, e.g., supported phosphoric acid catalysed, processes. These are primarily a lower average degree of branching, and a lower proportion of Type V olefins, making them more suitable for onward processing, e.g., higher alcohol, aldehyde, and acid manufacture, because of a desirable reactivity when the oligomeric composition is subjected to the oxo process (hydroformylation).

The present invention accordingly also provides an oligomeric hexene mixture having an average degree of branching of at most 0.95, especially one within the range of from 0.92 to 0.95, and a maximum Type V content of 6%, preferably 5%.

The present invention further provides an oligomeric nonene mixture having an average degree of branching of at most 2.0, and advantageously in the range of 1.5, preferably 1.78, to 2.0, more advantageously 1.78 to 1.86, and having a type V olefin content of at most 14%, preferably within the range of 10 to 14%, especially one obtainable by ZSM-22 catalysed oligomerization, especially in the presence of sulphur. Advantageously, the Type IV olefin content is within the range of 58 to 60%; advantageously the Type III olefin content is within the range of 7.25 to 7.75%; advantageously the Type II olefin content is within the range of 18.5 to 20%, and advantageously the Type I olefin content is 25 1.2to 2.2%.

The invention further provides an oligomeric dodecene mixture having an average degree of branching of at most 2.75, advantageously in the range of 2.70 to 2.75, and advantageously one having a type V olefin content of at most 19%, and preferably within the range of from 16 to 19%, especially one obtainable by ZSM-22 catalysed oligomerization, especially of propene, especially in the presence of sulphur. Advantageously, the type IV olefin content is within the range of 59 to 62%; advantageously the Type III olefin content is within the range 4.8 to 5.7%; and advantageously the Type II olefin content is within the range 14 to 15%.

As indicated above, the oligomers of the invention are especially suitable as feedstocks for further processing, including at least one of the following: fractionation; hydrogenation; hydroformylation; oxidation; carbonylation; etherification; epoxidation, and hydration. The hydrogenated oligomeric octenes may comprise, for example, 12 to 15% 2-methylheptane; 22 to 28% 3-methylheptane; and 7 to 9% 4-methylheptane. These are especially readily obtainable by oligomerization using a catalyst comprising ZSM-22.

The eventual products may be alcohols, produced for example by hydroformylation and hydrogenation; esters, in which the alcohols are esterified as with inorganic or organic acids, including carboxylic acids, especially polycarboxylic acids; aldehydes, acids, in which the hydroformylation products are oxidized and hydrogenated, and numerous other end uses.

The esters with polycarboxylic acids are especially valuable as plasticizers, and the invention further provides plasticizer compositions comprising the esters, and polymeric compositions, especially of vinyl polymers, more especially PVC, comprising the esters, and shaped structures formed of the plasticized polymeric compositions.

EXAMPLES

The following examples, in which parts and percentages are by weight unless otherwise indicated, illustrate the invention.

All feeds used in the examples were hydrated by passage through a water saturator at 250 to 40° C.

Olefin monomer conversion rates were derived from gas chromatographic analysis using peak areas normalized to the total sum of the paraffins in the feed as internal standard, conversion being expressed as:

$$\text{conversion \%} = 100\left[1 - \frac{A\ o.m./A\ \text{paraffins}}{A°\ o.m./A°\ \text{paraffins}}\right]$$

where A represents chromatographic peak area in product (wt %), A° represents chromatographic peak area in feed (wt %) and o.m. represents olefin monomer(s).

Selectivity to a given oligomer (dimer, trimer, etc.) is also determined from gas chromatographic peak areas, after hydrogenation of the product stream.

Example 1

In this example, butene oligomerization was carried out over a commercial ZSM-22 catalyst (ZSM-22 (75%) supported on alumina), at a weight hourly space velocity of 6.8 $h^{-1}$, on a 60 to 65% butenes/35 to 40% butane feedstock hydrated by passing through water at 40° C. The reactor effluent was analysed by gas chromatography (GC), feed and product olefin/paraffin ratios being compared to determine conversion. Liquid product was analysed on GC equipment having a platinum catalyst to hydrogenate olefins to paraffin, carbon number and skeleton being determined. In Comparative Samples C1 and C3 a pure (i.e., sulphur-free)

butene feed was used, in Comparative Sample C2 and Example 1 a refinery feedstock containing 20 ppm sulphur (16 ppm dimethylsulphide, 1.5 ppm diethyl sulphide, remainder methylethylsulphide and mercaptans) was used.

The results are shown in the table below.

| Sample | C1 | C2 | C3 | 1 |
|---|---|---|---|---|
| Sulphur, ppm | 0 | 20 | 0 | 20 |
| Temperature, °C. | 225 | 217 | 280 | 281 |
| Days On Steam | 7 | 7 | 13.6 | 13.6 |
| Total Conversion, % | 50.76 | 33.27 | 93.04 | 91.45 |
| Product Mix, % | | | | |
| $C_4$ | 2.5 | 2.58 | 2.7 | 1.62 |
| $C_5$ | 0.77 | 0.92 | 0.96 | 0.92 |
| $C_6$ | 0.15 | 0.14 | 0.41 | 0.37 |
| $C_7$ | 0.26 | 0.2 | 1.15 | 0.97 |
| $C_8$ | 66.11 | 71.66 | 50.77 | 52.48 |
| $C_9$ | 1.86 | 2.03 | 2.8 | 2.5 |
| $C_{10}$ | 0.63 | 0.66 | 1.9 | 1.81 |
| $C_{11}$ | | | | |
| $C_{12}$ | 17.21 | 13.69 | 25.8 | 25.29 |
| $C_{13}$ | 1 | 0.88 | 1.74 | 1.6 |
| $C_{14}$ | | | | |
| $C_{15}$ | | | | |
| $C_{16}$ | 9.51 | 7.24 | 11.78 | 12.44 |
| Sum | 97.5 | 97.42 | 97.31 | 98.38 |
| $C_7$–$C_9$, % | 70 | 76 | 56 | 57 |
| $C_{10}$–$C_{13}$, % | 19 | 16 | 30 | 29 |
| $C_{13}$+, % | 10 | 07 | 12 | 13 |
| $C_8/(C_7 + C_8 + C_9)$ | 96.9 | 97 | 92.8 | 93.8 |

Comparative Samples 1 and 2 show that catalyst activity is significantly reduced by the presence of sulphur at lower operating temperatures (about 220° C.) whereas as shown by Comparative Sample 3 and Example 1 the negative effects of sulphur are avoided at 280° C.

The carbon skeletons of the products, after hydrogenation, are shown in the table below.

| Example | C1 | C2 | C3 | 1 |
|---|---|---|---|---|
| Run | | | | |
| 2,2,4-tri-Me-pentane | 0.72 | 1.1 | 0.39 | 41 |
| 2,2-di-Me-hexane | 1.17 | 1.16 | 1.8 | 1.8 |
| 2,5-di-Me-hexane | 2.83 | 1.5 | 9.29 | 8.99 |
| 2,4-di-Me-hexane | 11.74 | 11.88 | 16.89 | 16.84 |
| 3,3-di-Me-hexane | 1.86 | 2.74 | 0.97 | 0.95 |
| 2,3,4-tri-Me-pentane | 3.66 | 5.28 | 1.61 | 1.76 |
| 2,3,3-tri-Me-pentane | 0.95 | 1.5 | 3 | 0.32 |
| 2,3-di-Me-hexane | 6.29 | 6.44 | 8.61 | 8.75 |
| 2-Me-3-Et-pentane | 2.77 | 3.62 | 2.02 | 2.08 |
| 2-Me-heptane | 13.17 | 9.34 | 14.22 | 14.15 |
| 4-Me-heptane | 7.48 | 5.27 | 7.85 | 7.8 |
| 3,4-di-Me-hexane | 18.57 | 28.75 | 6.17 | 6.47 |
| 3-Me-heptane | 23.63 | 17.11 | 24.73 | 24.55 |
| n-Octane | 5.15 | 4.32 | 5.17 | 5.11 |
| $C_8$ Linear | 5.15 | 4.32 | 5.17 | 5.11 |
| $C_8$ Mono-branched | 44.27 | 31.72 | 46.8 | 46.5 |
| $C_8$ Di-branched | 45.24 | 56.08 | 45.74 | 45.89 |
| $C_8$ Tri-branched | 5.34 | 7.88 | 2.29 | 2.49 |
| $C_8$ Branchiness | 1.51 | 1.68 | 1.45 | 1.46 |

Example 2

This example illustrates the influence of sulphur on the activity of a ZSM-57 catalyst in propene oligomerization and the effect of an elevated temperature on that influence.

A 50% ZSM-57/50% alumina catalyst was used to oligomerize a sulphur-free feedstock of 50% propene/50% butanes at 135° C., at a WHSV of 2.02. The product stream contained about 73% nonenes, 9% dodecenes and 7% hexenes at a total conversion rate of 88%, average degree of branching of the nonenes 1.99.

2 ppm of dimethyldisulphide were added to the feedstock and the run continued under otherwise the same conditions. Over the course of 24 hours, the catalyst was nearly completely deactivated, shown by a fall in the conversion rate to 5%.

The temperature was then raised to 175° C., when the catalyst recovered and the conversion rate rose to 95%. The product stream contained about 64% nonenes, 11% dodecenes and 5% hexenes, average degree of branching of the nonenes 1.95.

The example shows that an elevated temperature avoids the deleterious effects of sulphur on the activity of the crystalline molecular sieve catalyst, and is effective to re-activate a de-activated catalyst.

Example 3

To the pure feedstock of Example 2 were added 7 ppm ethyl sulphide and oligomerization was carried out at 168° C. over the catalyst used in that example. The product stream contained about 66% nonenes, 11% dodecenes and 9% hexenes, branchiness of the nonenes 2.0. The conversion rate was 93%.

It was found, using sulphur-free feed, that oligomerizing propene over ZSM-22 at 255° C. yielded a nonene product of branchiness 1.57, with 40% of mono-branched isomers. Similarly, using ZSM-22 at 277° C., a sulphur-free butene feed yielded an octene product of branchiness 1.15, with 66% mono-branched isomers. A sulphur-containing feedstock would yield similar results.

We claim:

1. A process for the oligomerization of an olefinic feedstock which comprises contacting under oligomerization conditions, said oligomerization conditions including an oligomerization reaction temperature, an olefinic feedstock containing of from 1 to 100 ppm by volume of at least one sulphur-containing component with a catalyst comprising at least one crystalline molecular sieve selected from sieves of the TON and MFS structure types, and recovering a product containing at least one olefin oligomer, wherein said process is further characterized by a step of increasing said oligomerization reaction temperature in response to an increase in the presence of said at least one sulfur-containing component in said feedstock.

2. A process as claimed in claim 1, wherein the feedstock comprises at least one olefin having from 2 to 12 carbon atoms.

3. A process as claimed in claim 2, wherein the feedstock comprises at least one alkene selected from propene and butenes.

4. A process as claimed in claim 1, carried out at a temperature of at least 160° C.

5. A process as claimed in claim 4, carried out using a catalyst comprising an MES structure type molecular sieve.

6. A process as claimed in claim 5, carried out at least 170° C.

7. A process as claimed in claim 5, carried out at least 220° C.

8. A process as claimed in claim 1, wherein the crystalline molecular sieve is H-ZSM-57.

9. A process as claimed in claim 4, carried out using a catalyst comprising a TON structure type molecular sieve at a temperature of at least 200° C.

10. A process as claimed in claim 9, carried out at a temperature of at least 220° C.

11. A process as claimed in claim 9, carried out at a temperature of at least 250° C.

12. A process as claimed in claim 1, wherein the crystalline molecular sieve is H-ZSM-22.

13. A process as claimed in claim 8, wherein the crystalline molecular sieve comprises a mixture of H-ZSM-22 and H-ZSM-57.

14. A process as claimed in claim 1, wherein the content of said at least one sulphur-containing component is within the range of 1 to 50 ppm by volume in said feedstock.

15. A process as claimed in claim 14, wherein said content is within the range of 1 to 30 ppm in said feedstock.

16. A process as claimed in claim 14, wherein said content is within the range of 1 to 20 ppm.

17. A process as claimed in claim 1, wherein said at least one sulphur-containing component comprises at least one compound selected from hydrogen sulphide, dimethyl sulphide, diethyl sulphide, ethyl methyl sulphide, n-propyl sulphide, 1- and 2-propanethiols, 1-butanethiol, 1,1-methylethylthiol, ethyl methyl disulphide, dimethyl disulphide and tetrahydrothiophene.

18. A process as claimed in claim 1, wherein the feedstock is hydrated.

19. A process as claimed in claim 1, wherein the feedstock is or comprises an oligomer.

20. The process of claim 1, including:
(a) obtaining a decrease in the conversion rate of said oligomerization in response to said increase in the presence of said at least one sulfur-containing component in said feedstock; and then
(b) increasing said oligomerization reaction temperature and obtaining an increase in said conversion rate in response to said increase in said oligomerization reaction temperature.

21. The process of claim 20, wherein the at least one sulfur-containing component in step (b) is present in the amount of 2–20 ppm by volume of said feedstock.

22. A process for the oligomerization of an olefinic feedstock which comprises contacting under oligomerization conditions, said oligomerization conditions including an oligomerization reaction temperature, an olefinic feedstock with at least one crystalline molecular sieve selected from sieves of the TON and MFS structure types, and recovering a product containing at least one olefin oligomer, wherein said process is characterized by a step of increasing the oligomerization reaction temperature in response to an increase in the presence of at least one sulfur-containing component in said feedstock.

23. The process of claim 22, further characterized by:
(a) obtaining a decrease in the conversion rate of said oligomerization in response to an increase in the presence of a sulfur-containing component in said feedstock; and then
(b) increasing said oligomerization reaction temperature and obtaining an increase in said conversion rate in response to said increase in said oligomerization reaction temperature.

* * * * *